(12) United States Patent  (10) Patent No.: US 6,299,567 B1
Forrest et al.  (45) Date of Patent: Oct. 9, 2001

(54) SELECTIVE COMPONENT AGITATION APPARATUS AND METHOD

(75) Inventors: Gordon Coulter Forrest, East Horsley; Gerald John Allen, Windlesham; Philip Missing, Ashford, all of (GB)

(73) Assignee: Alfa Wasserman S.p.A. (IT)

( * ) Notice: Subject to any disclaimer, the term of this patent is extended or adjusted under 35 U.S.C. 154(b) by 0 days.

(21) Appl. No.: 08/725,529

(22) Filed: Oct. 3, 1996

Related U.S. Application Data

(63) Continuation of application No. 08/412,844, filed on Mar. 29, 1995, now abandoned, which is a continuation of application No. 08/277,348, filed on Jul. 19, 1994, now abandoned, which is a continuation of application No. 08/129,916, filed on Sep. 30, 1993, now abandoned, which is a continuation of application No. 07/631,130, filed on Dec. 20, 1990, now abandoned.

(30) Foreign Application Priority Data

Dec. 22, 1989 (GB) .................................................. 8929121
Sep. 18, 1990 (GB) .................................................. 9020352

(51) Int. Cl.$^7$ ................................................. G01N 33/543
(52) U.S. Cl. ........................... 482/64; 366/220; 422/102; 435/287.3; 436/45
(58) Field of Search ................ 422/63–67, 102; 436/45; 435/287.2, 287.3, 288.1; 366/220, 224, 232

(56) References Cited

U.S. PATENT DOCUMENTS

| 4,120,662 | 10/1978 | Fosslein . | |
|---|---|---|---|
| 4,268,268 | * 5/1981 | Blum | 436/52 |
| 4,318,884 | * 3/1982 | Suzuki . | |
| 4,477,578 | * 10/1984 | Miles et al. | 436/518 |
| 4,595,562 | * 6/1986 | Liston | 422/65 |
| 4,808,380 | 2/1989 | Minekane . | |
| 4,826,319 | 5/1989 | Namba et al. . | |
| 4,848,917 | * 7/1989 | Benin et al. | 422/99 |
| 4,849,177 | 7/1989 | Jordan . | |
| 4,855,909 | 8/1989 | Vincent et al. . | |
| 5,098,845 | 3/1992 | Babson . | |
| 5,132,088 | 7/1992 | Wakatake . | |

FOREIGN PATENT DOCUMENTS

| 0329183 | * 8/1989 | (EP) . |
|---|---|---|
| 2 081118A | 2/1982 | (GB) . |
| 89/10785 | 11/1989 | (WO) . |

* cited by examiner

*Primary Examiner*—Jan Ludlow
(74) *Attorney, Agent, or Firm*—Hamilton, Brook, Smith & Reynolds, P.C.

(57) ABSTRACT

An independently rotatably mounted container may be used, by agitating the contents thereof, in the performance of a multi-component reaction or assay, by selective rotation of said container in the presence of adjacently mounted component containers which are not rotated. Such a principle may be applied in suspending solid phases in, for example, automated immunoassay apparatus or in reconstituting freeze dried reagents. Selective rotation has a number of advantages including gentleness to components and greater efficiency and reliability.

14 Claims, 3 Drawing Sheets

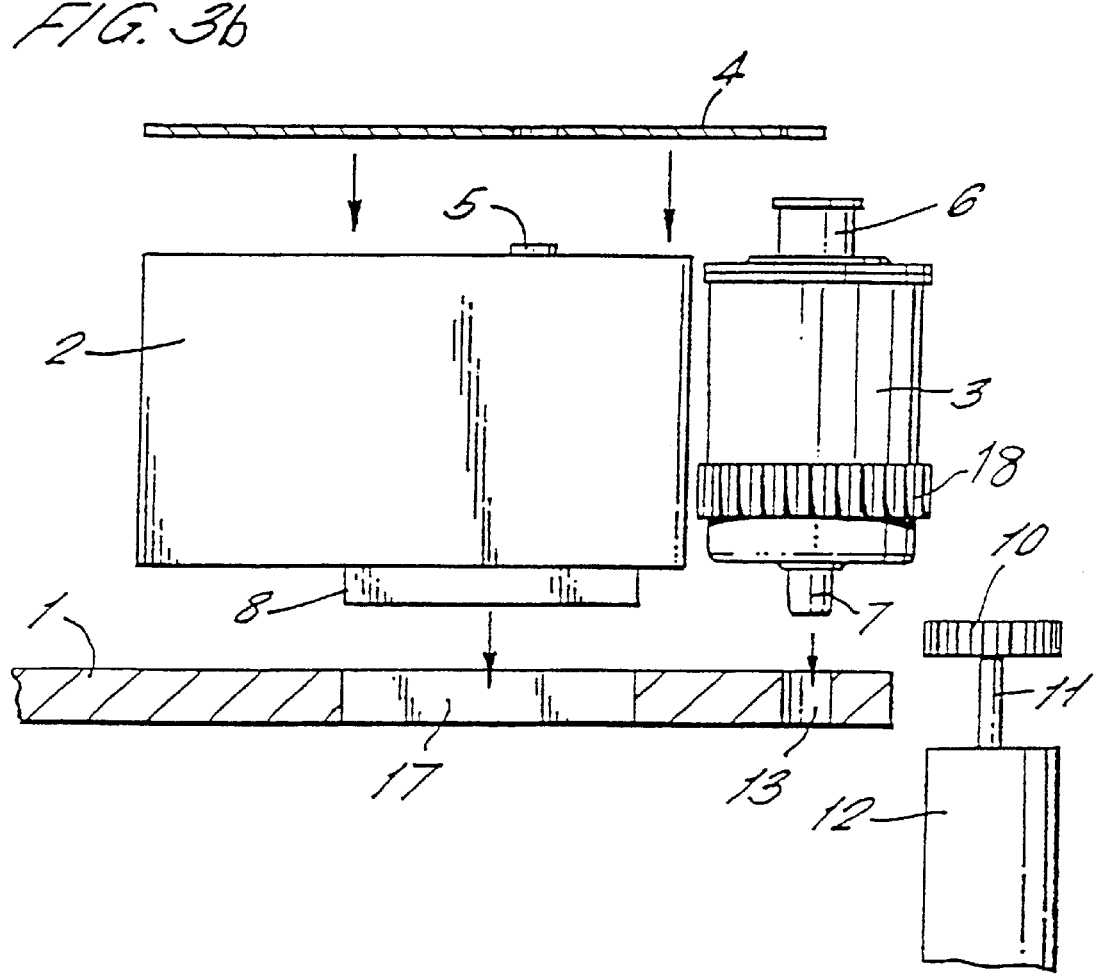

SELECTIVE COMPONENT AGITATION APPARATUS AND METHOD

RELATED APPLICATION

This application is a continuation of application Ser. No. 08/412,844 filed Mar. 29, 1995 (now abandoned), which is a File Wrapper Continuation of 08/277,348 filed Jul. 19, 1994, (now abandoned), which is a File Wrapper Continuation of 08/129,916 filed Sep. 30, 1993 (now abandoned), which is a Continuation of 07/631,130 filed Dec. 20, 1990 (now abandoned), which claims priority to British Patent Application No. 89 29121.5 filed Dec. 22, 1989 and British Patent Application No. 90 20352.2 filed Sep. 18, 1990.

BACKGROUND OF THE INVENTION

This invention relates to selective component agitation apparatus and method, e.g. apparatus for suspending the solid phase component in solid phase-containing reaction systems or reactants, particularly in assay reaction systems. The apparatus is particularly useful in automated assay machines. The invention further relates to a method for carrying out solid phase resuspension.

It is usual in, for example, hospital laboratories, to carry out large numbers of diagnostic reactions on samples from one or more subjects. Such reactions are conveniently carried out using automated assay machines, programmed to carry out the necessary tests and to display and/or issue the results in some hard copy form.

Usually such machines are provided with carriers, for example racks or carousels, which hold containers with the necessary reaction components for one or more specific diagnostic tests and/or the samples to be tested themselves.

Many assays, particularly where the assay is an immunoassay, have a solid component on which a particular reagent may be bound or adsorbed. In many cases the solid component is a particulate or finely divided solid phase which is capable of suspension in aqueous media. It is of course desirable, prior to using such solid phase components, to ensure that they are adequately suspended, thus preventing inaccuracies from being introduced into the assay.

It is known in the art to mix or resuspend components by vibratory methods, for example vibratory mixers are well known which operate by placing a sample container on a vibrating element, which causes mixing in the sample. One commercial immunoassay system uses a reaction container which is suspended at its top by a resilient "web". The base of the container is not suspended but hangs "free", and is adapted to interact with a mechanical agitator to transmit a disturbance to the whole container. In addition, EP 0051341 discloses an apparatus which includes a reagent/sample container-carrying carousel, which carousel is rotatable and has mounted thereon in fixed positions a number of individual containers.

In many systems found in the art, a problem with reactions which comprise a solid phase component is the cumulative effects of frequent resuspension and/or disturbance on the useful life of the solid phase reagent. After a time, solid phase components deteriorate due to fragmenting of particles or loss of bound reagent. This is a particular problem where, as is usually the case, a carousel carrier supports components for different tests, not all of which will be required for a particular patient sample, and some of which may be infrequently used and thus the corresponding reactants infrequently replenished. In such a situation, systems which vibrate or otherwise disturb the whole carousel carrier will cause resuspension of all solid phases carried thereon, regardless of whether or not these are needed for a particular reaction or test, leading to reactant deterioration and, ultimately, inaccurate or poor results. There are further problems in the art, in that suspension caused by vibration is unreliable and may also lead to inaccurate or poor results, and such a mixing or suspension made may result in undesirable aeration or frothing.

SUMMARY OF THE INVENTION

The present invention provides apparatus for selectively agitating one or more components of a multi-component reaction or assay, which apparatus comprises at least one container for said one or more components which is rotatably mounted upon a platform also carrying other component containers, said at least one container being mounted so as to be free to rotate independently of other containers on the platform, and means for selectively rotating said at least one container.

The present invention in a preferred embodiment provides apparatus for suspending a particulate solid phase which is suspensible in aqueous media, which apparatus comprises at least one container for said solid phase carried upon a platform which also carries reagent-, reaction-, and/or sample-containers, said at least one container being mounted so as to be free to rotate independently of other containers on the platform, and means for selectively rotating said at least one container. Preferably, the apparatus is part of an automated immunoassay system, the platform being a carousel carrying containers for use in a number of immunoassay tests. In especially preferred embodiments, there is one of said selectively rotatable solid phase containers for each immunoassay test.

The rotatable selectively solid phase container(s) may be mounted on bearings facilitating ease of rotation, e.g. PTFE or polypropylene or other low-friction plastics material bearings. The container(s) themselves may be made of such materials, eliminating the need for special bearings due to the resulting low frictional coefficient surface of the container(s). Such container(s) may be provided with a specifically shaped base rotatably to fit into a corresponding hole or recess on a platform.

Preferably, the means for selective rotating solid phase container(s) comprises a motor which can drive the container either directly or indirectly. An individual motor may be provided for each independently rotatable solid phase container, or a single motor operable with each such container may be used.

The preferred type of platform is a rotatable carousel which is adapted to carry the containers, and which by simple rotation can bring a required solid phase container into alignment with a fixed position motor drive, thereby allowing the selective rotation of a solid phase container independently of other containers on the carousel.

If desired, other containers may be positioned and mounted so as to be selectively rotatable.

Rotatable containers can be rotated via a wheel mounted on a drive shaft attached to the appropriate motor. The container is brought into frictional contact with the wheel whereby when the motor is energized and the wheel turns the container is rotated. Alternatively, the container may carry an integral gear wheel around its circumference, e.g. moulded into a lower part of the circumference, which gear meshes with a drive gear on the drive shaft.

The present apparatus can also include means to monitor spinning of the container(s), e.g. via a fixed sensor aligned to detect reflected light from a reflective area provided on the container(s). The invention also envisages the possibility of monitoring the degree of resuspension of solid phase by employing one or more transparent rotatable containers and measuring of a light absorption or scatter beam passing through such containers. In general, positive feed back may be provided to a computer controlling apparatus including the rotatable container(s) of the invention, e.g. either by a Hall effect device or by a reflective opto device to ensure that the solid phase is adequately spun. These two sensors may be of the type supplied by RS Components Ltd.

The solid phase containers envisaged in the present invention can be provided separately or as part of complete modules comprising several vessels, e.g. one or more liquid reagent containers together with one or more solid phase containers, wherein in each module the containers are preferably all joined by an overlaying snap fit top adapted to link the containers and to hold them in the correct alignment for mounting on the platform. If desired, at least some of the reagent containers can be provided in integral form as a one piece moulding. In such circumstances a top for linking purposes may not be necessary.

In addition, the present apparatus can be provided with means to cover or seal access openings of containers, whether solid phase containers or other vessels, while they are not in use. Such means can include, inter alia, foil or plastics material seals or removable plugs or caps. A single cover can be employed for a number of containers simultaneously. The means can comprise a movable cover which, when a particular container is not specifically required, may be positioned such that the access opening of such container is covered. Such a movable cover can be adapted to cover or seal the access openings of all containers in at least one module, including the solid phase container or containers. Movement of the cover can be linked to control of the positioning of the solid phase container or its rotation means.

In general, the invention provides the use of an independently rotatably mounted container in agitating the contents thereof, e.g. for mixing or suspension purposes, in the performance of a multi-component (i.e. two or more component) reaction or assay, by selective rotation of said container in the presence of-adjacently mounted component containers which are not rotated. In one embodiment, the invention provides such a use when applied to the reconstitution of a freeze dried reagent by loading said container with the freeze dried reagent and reconstitution fluid therefor and effecting said selective rotation. This means of reconstitution of freeze dried reagents, which are often quite unstable, using reconstitution fluids therefor in accordance with normal practice, is a very effective means of achieving dissolution of such reagents.

In a further preferred aspect, the invention provides the use of an independently rotatably mounted solid phase container in suspending a particulate solid phase suspensible in aqueous media, in the performance of a multi-component reaction or assay, by selective rotation of said container in the presence of adjacently mounted reagent-, reaction-, and/or sample- containers which are not rotated.

Spinning or rotation of the container need not be confined to a single spin cycle in a single direction. Several cycles of rotation can be used, first in one direction and then in the reverse direction. In addition, the speed of rotation can be variable in order to ensure efficient resuspension for different types of solid phase.

The present invention provides, inter alia, the following advantages compared to existing systems.

a) It avoids the need to provide, for instance, a special diaphragm to transmit vibration to agitate container content.
b) Contact between container and agitation mechanism is more critical with methods depending upon other methods, e.g. vibration.
c) Individual containers can be spun to achieve, for instance, solid phase resuspension at will selectively and without agitating adjacent containers and their contents.
d) Rotation or spinning is simple and reliable mechanically.
e) A high degree of mixing control is possible with spinning or rotation, through speed and duration of rotation, rate of acceleration/deceleration, direction of rotation etc. Spinning or rotation raises a solid phase into the body of the suspending fluid. By stopping rotation, then rotating in the opposite direction, highly efficient resuspension can be achieved very quickly and controllably. Further refinements can be made by providing baffles or other obstructions in the container which is to be spun.
f) Aeration of reagent is minimised with spinning, thus minimising microscopic or surface bubbles, and frothing, and reducing the tendency to inaccurate or poor results.
g) Spinning or rotation is a 'gentle' means of agitation, hence:
  i) less likelihood of fragmenting soft or fragile particles (particles may be composed of loosely bound aggregates of smaller particles);
  ii) less likelihood of denaturing sensitive proteins e.g. antibodies, attached to solid surfaces; and
  iii) less likelihood of creating variable populations of very small particles (fines) which may not sediment within the timeframe available on an automated assay instrument.
h) Engineering of apparatus is simplified since a spinning vessel can be made from a 'slippery' material such as plastics material, e.g. PTFE or polypropylene, to create 'self-lubricating' bearings.
i) Monitoring of spinning, and the resulting degree of solid phase suspension, can be easily and effectively achieved in an automated apparatus.

In what follows, the invention will be described with reference to automated immunoassay equipment. The invention is not, however, limited to such an application.

BRIEF DESCRIPTION OF THE DRAWINGS

FIG. 3b is similar to FIG. 3a, but shows a different mechanism for driving container rotation.

DESCRIPTION OF PREFERRED EMBODIMENTS

Figure 1:
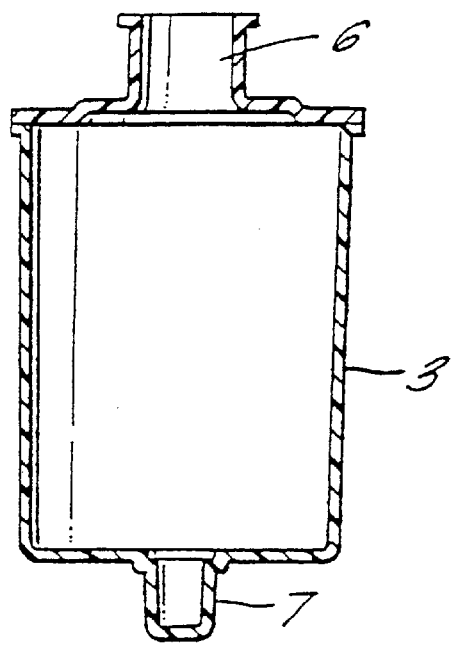
FIG. 1 is a cross-section of an immunoassay apparatus solid phase container usable in the invention.

FIG. 1 shows a solid phase container 3, suitable as a reagent vessel in an automated immunoassay system. Container 3 has access opening 6, from which its contents may be withdrawn, and a shaped base portion 7, adapted to slot into a corresponding hole or recess in a support platform (not shown in this Figure). One preferred material of construction of such a container 3 is polypropylene due to its low frictional coefficient, strength and low mass.

Figure 2:
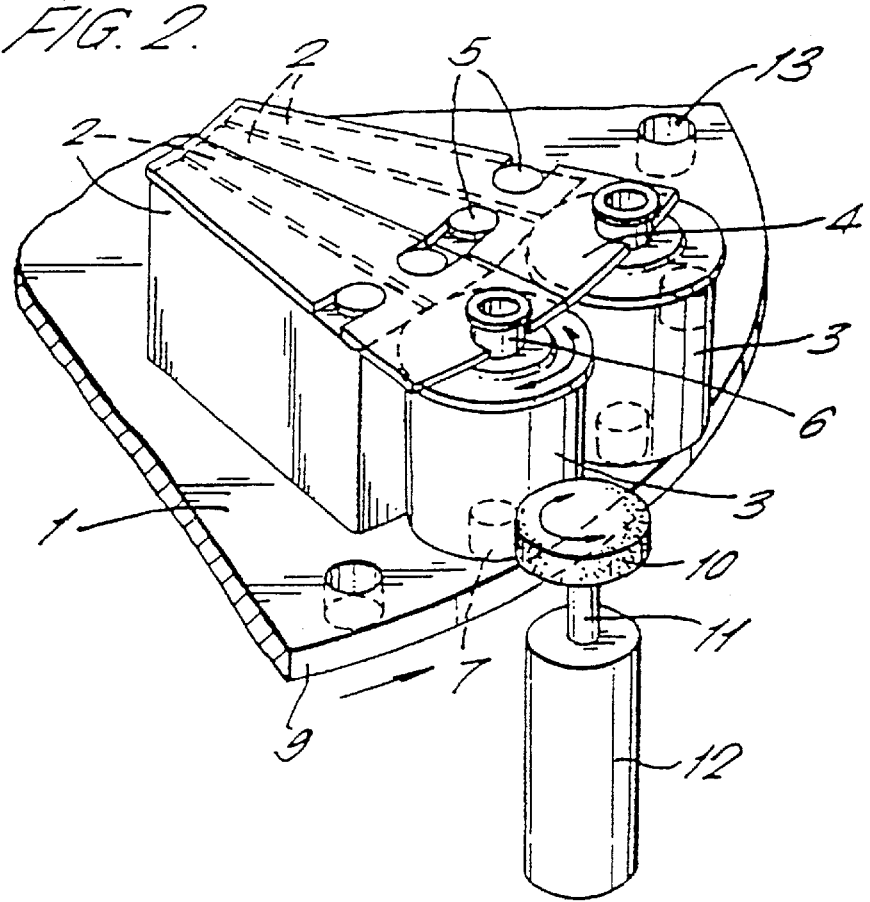
FIG. 2 is a perspective view showing part of an immunoassay apparatus embodiment of the invention in which a carousel platform is provided, on which are mounted reagent "packs" and solid phase or reaction containers.

In FIG. 2, a portion of an automated immunoassay machine carousel platform 1 is shown, carrying reagent containers 2, and container 3 as shown in FIG. 1. Carousel 1 may be rotated by means not shown (in the direction of the arrow).

In the apparatus of FIG. 2, means for selectively rotating the solid phase containers 3 consists of a motor arrangement 12 which drives a wheel 10 via a drive shaft 11. Motor arrangement 12 may be in a fixed position or movable, and, with or without movement of motor arrangement 12, the carousel 1 may be rotated to bring wheel 10 into frictional contact with a desired container 3 such that powered rotation of wheel 10 causes the desired solid phase container 3 to rotate. Each base portion 7 of container 3 fits into a corresponding recess 13 adjacent the periphery 9 of carousel 1. Due to the "slippery" nature of containers 3, they are able to rotate in recesses 13.

Reagent containers 2 having access openings 5 mounted on carousel 1 are provided as "packs" consisting of two reagent containers 2 together with a corresponding solid phase or reaction container 3. Containers 2 and 3 are held together by a snap-fit pack top 4 which fits over reagent container access openings 5 and the respective solid-phase container access opening 6 without obstruction. In addition, rotation of container 3 is not impeded by the nature of the fit.

In operation of the apparatus, bringing a desired container 3 into contact with wheel 10 allows that container 3 to be selectively spun or rotated, this causing the suspension of any solid phase contained therein but without moving adjacent containers. Furthermore, after any given test (and a pack of two reagent containers 2 and one container 3 are usually associated with one particular immunoassay test), rotation of carousel 1 to a position corresponding to the next desired test allows wheel 10 selectively to rotate the appropriate next container 3 when desired. The illustrated immunoassay apparatus will in operation also require conventional pipetting or aspirating means (not shown) for moving reagents from container to-container, dependent upon the precise test be carried out. Normal computer control systems programmed to provided a desired sequence of operations can also be included (not shown).

Figure 3A:
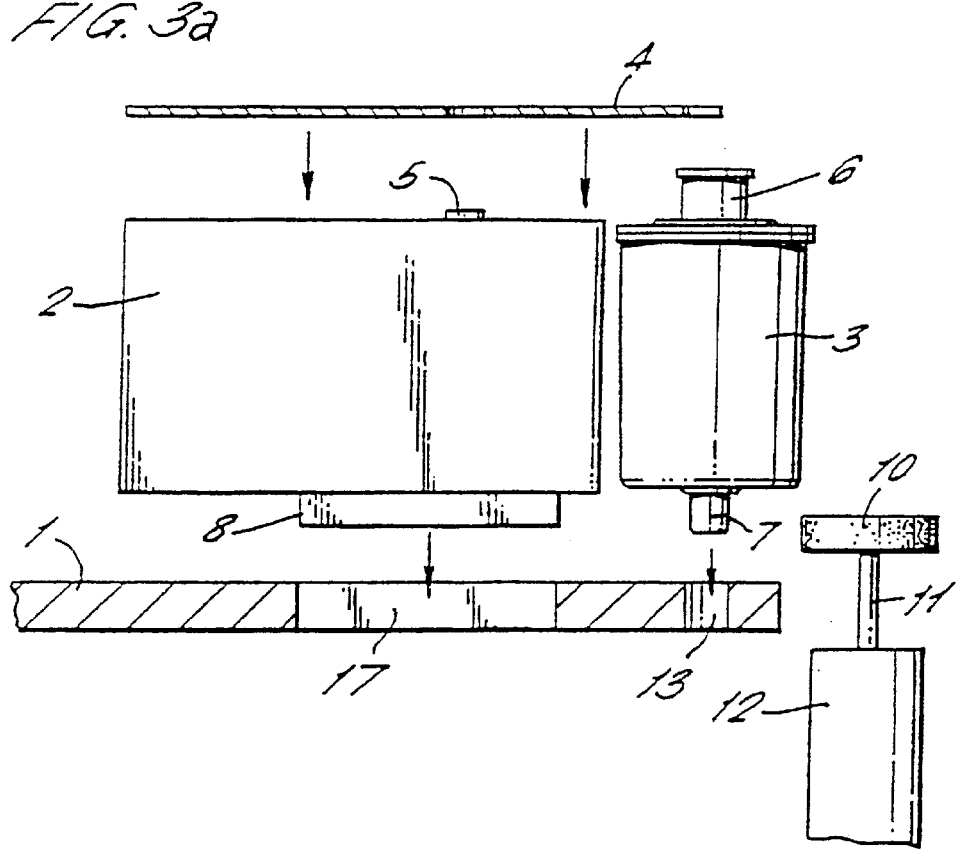
FIG. 3a is an exploded side elevation and partial cross-section showing the arrangement of various components of the embodiment of FIG. 2.

FIG. 3a shows more clearly how reagent containers 2, a solid phase container 3 and pack top 4 interfit. The resulting combination can be termed a test or reagent "pack". Complete packs can be supplied for particular immunoassay tests, and individual containers can be replaced as desired by removing pack top 4. Such packs are removably mounted on the carousel 1 by reagent container formed base portions 8 and solid phase container base portions 7 fitting into corresponding recesses 17 and 13, respectively, in carousel 1. The solid phase container 3 is free to rotate in its mount. If desired, special bearings (not shown) can be positioned in recess 13 to facilitate such rotation. Such a bearing can take the form of an annulus (not shown) of low frictional coefficient plastics material.

In FIG. 3b, an alternative embodiment is illustrated in which wheel 10 is provided in the form of a gear wheel adapted to mesh with gear track 18, which track is integrally moulded into the lower circumference of container 3. This permits a surer engagement between wheel 10 and container 3, and hence a more reliable transmission of the drive from motor 12.

Figure 4:
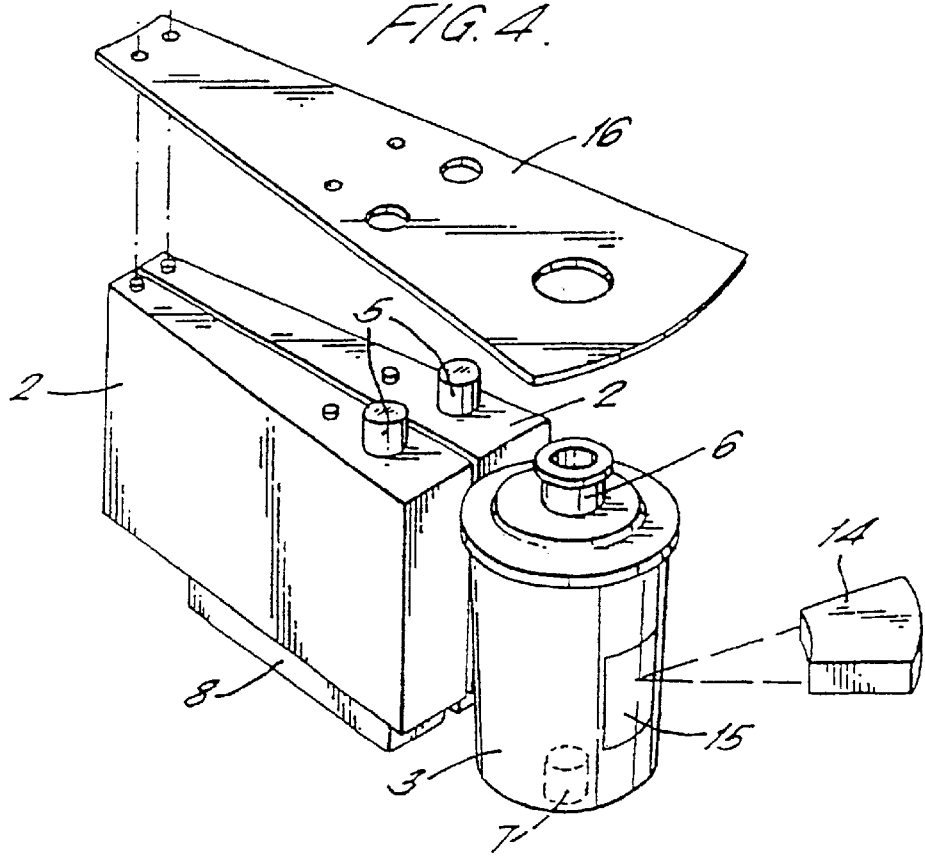
FIG. 4 is a partially exploded perspective view of an alternative reagent pack usable in the invention and including means for monitoring container spinning.

FIG. 4 shows the components of another container pack of the invention consisting of reagent containers 2, a solid phase container 3 which, in use, can be selectively rotated independently of the other containers, and a snap on reagent pack top 4 which differs from that shown in FIG. 2 in that it is not cut away. The skilled man will appreciate that the precise configuration of the pack top is unimportant, only that such a pack top should allow the various containers to be linked together in the desired orientation while also allowing free access to the said containers. If desired the pack top can, for example, carry strengthening such as reinforcing ribs. It will also be appreciated that, if desired for engineering simplicity, pairs of containers 2 shown in the various Figures can be in the form of a single piece moulding, perhaps eliminating the need for a pack top.

The embodiment of FIG. 4 also includes means whereby rotation of solid phase containers 3 can be monitored, comprising a reflective area 15 located on the solid phase container 3 and a fixed sensor 14 for picking up reflected light. The frequency of light pick up is proportional to the speed of rotation. Such an arrangement is especially useful in automated assay machines.

Thus, the apparatus of the present invention allows selective suspension of a solid phase component of a solid phase-containing reaction system without disturbing containers carrying other components which are present on the same platform or carrier. This is particularly useful when the reactions in question are those performed by an automated assay system, which systems are usually designed to carry out many different test reactions, each of which may have a different solid phase component. However, the invention is not limited to such systems. Selective suspension of only those solid phase components required at a particular time may be achieved, thereby increasing the useful life of individual reaction components.

As can be appreciated, whilst the invention provides a flexible solution to the problems noted above, it is also readily adaptable to particular requirements in terms of type of suspension cycle, number of reaction components for a given reaction, type of container platform, use with different forms of automated machinery, and so on.

Although the invention has been generally described above, and preferred embodiments have been disclosed in detail, the skilled reader will readily appreciate variations, alterations and modifications of the invention which do not depart from the spirit and scope of the present invention as defined in the appended claims.

We claim:

1. An apparatus for selectively agitating one or more components of a multi-component reaction or assay, which apparatus comprises at least one component container which is rotatably mounted upon a platform which carries a multiple number of component containers, said at least one component container having an access opening via which the contents of the component container can be accessed and being mounted so as to be free to rotate independently of other component containers on the platform, and means for selectively rotating each of said at least one component container independently so as to cause agitation of the contents thereof, wherein said rotating means does not physically obstruct access to said access opening, and wherein said at least one container is provided, together with one or more additional containers, as a container pack which is removably mounted on said platform.

2. The apparatus of claim 1 wherein said apparatus is part of an automated immunoassay system.

3. An apparatus for suspending a particulate solid phase which is suspensible in aqueous media, which apparatus comprises at least one container containing said particulate solid phase, said at least one container rotatably mounted upon a platform which carries one or more additional containers selected from the group consisting of reagent-, reaction-, and sample-containers, said at least one container having an access opening via which the contents of the container can be accessed and being mounted so as to be free to rotate independently of said additional containers on the platform, and means for selectively rotating each of said at least one container independently so as to bring said particulate solid phase into suspension therein, wherein said rotating means does not physically obstruct access to said access opening, and wherein said at least one container is provided, together with one or more additional containers, as a container pack which is removably mounted on said platform.

4. The apparatus of claim 3 wherein said platform is a rotatably mounted substantially circular carousel.

5. The apparatus of claim 3 wherein said at least one container is constructed of a material which facilitates ease of rotation of said container.

6. The apparatus of claim 3 wherein said means for selectively rotating said at least one container comprises a motor-powered drive carrying a drive wheel to be brought into frictional contact with said at least one container so as to rotate the same.

7. The apparatus of claim 3 wherein said means for selectively rotating said at least one container comprises a motor-powered drive carrying a drive wheel which wheel has a geared circumference, said at least one container having a gear track positioned around the periphery thereof and adapted to mesh with said drive wheel geared circumference.

8. The apparatus of claim 3 wherein said one or more additional containers constituting said pack being linked together by a pack top which fits over the containers in said pack without impeding the capability of said at least one container to rotate.

9. The apparatus as of claim 3 wherein said at least one container has a reflective area located on the exterior thereof and said apparatus also includes a sensor for monitoring light reflection thus permitting monitoring of the rotation of said at least one container.

10. The apparatus of claim 3 wherein said at least one container is transparent and the apparatus further includes means for monitoring solid phase suspension therein by measuring absorption or scatter of a light beam passed through said at least one container.

11. The apparatus of claim 3 wherein said apparatus is part of an automated immunoassay system where more than one separate immunoassay test is performed.

12. The apparatus of claim 11 having a multiple number of said at least one containers wherein each one of said multiple number contains said particulate solid phase and is rotatably mounted upon said platform.

13. The apparatus of claim 3 wherein said at least one container is rotatably mounted on said platform with a bearing which facilitates ease of rotation of said container.

14. An apparatus for selectively suspending a particulate solid phase which is suspensible in aqueous media, which apparatus comprises a platform, a discrete container module removably mounted on said platform wherein said discrete container module includes at least one component container and at least one rotatably mounted container containing said particulate solid phase, and means for selectively rotating said at least one rotatably mounted container independently so as to suspend said particulate solid phase, further wherein said at least one rotatably mounted container has a cover with an access opening via which the contents of said at least one rotatably mounted container can be accessed.

* * * * *